(12) United States Patent
Willis

(10) Patent No.: US 7,872,188 B2
(45) Date of Patent: Jan. 18, 2011

(54) METHOD AND APPARATUS FOR PERSONAL EXERCISE TRAINER

(76) Inventor: Mariann Martin Willis, 39 Elm Ave., Metuchen, NJ (US) 08840

( * ) Notice: Subject to any disclaimer, the term of this patent is extended or adjusted under 35 U.S.C. 154(b) by 179 days.

(21) Appl. No.: 12/408,025

(22) Filed: Mar. 20, 2009

(65) Prior Publication Data

US 2010/0236385 A1 Sep. 23, 2010

(51) Int. Cl.
*G10H 1/40* (2006.01)
(52) U.S. Cl. .................... 84/611; 84/600; 84/609; 84/610; 84/615; 84/616; 84/649; 84/650; 84/651; 84/653; 84/654
(58) Field of Classification Search .................. None
See application file for complete search history.

(56) References Cited

U.S. PATENT DOCUMENTS

| | | | | |
|---|---|---|---|---|
| 7,618,347 B2* | 11/2009 | Yeo et al. | ............. | 482/8 |
| 7,683,252 B2* | 3/2010 | Oliver et al. | ............. | 84/612 |
| 7,705,230 B2* | 4/2010 | Bowen | ............. | 84/612 |
| 7,728,214 B2* | 6/2010 | Oliver et al. | ............. | 84/612 |
| 7,745,716 B1* | 6/2010 | Murphy | ............. | 84/612 |
| 2006/0107822 A1* | 5/2006 | Bowen | ............. | 84/612 |
| 2007/0049461 A1* | 3/2007 | Kim et al. | ............. | 482/8 |
| 2007/0074617 A1* | 4/2007 | Vergo | ............. | 84/612 |
| 2007/0074618 A1* | 4/2007 | Vergo | ............. | 84/612 |
| 2007/0074619 A1* | 4/2007 | Vergo | ............. | 84/612 |
| 2007/0113725 A1* | 5/2007 | Oliver et al. | ............. | 84/612 |
| 2007/0113726 A1* | 5/2007 | Oliver et al. | ............. | 84/615 |
| 2009/0139389 A1* | 6/2009 | Bowen | ............. | 84/636 |
| 2009/0156887 A1* | 6/2009 | Hsu | ............. | 600/27 |
| 2009/0178542 A1* | 7/2009 | Jochelson et al. | ............. | 84/609 |
| 2009/0319230 A1* | 12/2009 | Case et al. | ............. | 702/182 |
| 2010/0168879 A1* | 7/2010 | Takatsuka et al. | ............. | 700/94 |
| 2010/0179389 A1* | 7/2010 | Moroney et al. | ............. | 600/301 |
| 2010/0186578 A1* | 7/2010 | Bowen | ............. | 84/612 |
| 2010/0188405 A1* | 7/2010 | Haughay et al. | ............. | 345/440 |
| 2010/0192754 A1* | 8/2010 | Kim et al. | ............. | 84/611 |
| 2010/0210421 A1* | 8/2010 | Case et al. | ............. | 482/8 |
| 2010/0251877 A1* | 10/2010 | Jochelson et al. | ............. | 84/609 |

OTHER PUBLICATIONS

"Longitudinal Modeling of the Relationship between Age and Maximal Heart Rate", pp. 822-829, Ronald L. Gellish, et al.,, copy 2007 by the American College of Sports Medicine.

* cited by examiner

*Primary Examiner*—Marlon T Fletcher
(74) *Attorney, Agent, or Firm*—Walter J. Teneza, Jr.

(57) ABSTRACT

Determining a plurality of heart rate sections for an individual, and selecting a plurality of songs, wherein each of the plurality of songs has an average beats per minute approximately equal to an average beats per minute of one of the plurality of heart rate sections, and playing the plurality of songs in a sequence on a song playing device. The plurality of songs includes a middle song, which has an average beats per minute which is greater than the average beats per minute of all of the other songs of the plurality of songs. The plurality of songs includes one or more preceding songs which precede the middle song, and each of which has an average beats per minute which is less than the average beats per minute of the middle song. The plurality of songs includes one or more succeeding songs which succeed the middle song, and each of which has an average beats per minute which is less than the average beats per minute of the middle song.

20 Claims, 4 Drawing Sheets

METHOD AND APPARATUS FOR PERSONAL EXERCISE TRAINER

FIELD OF THE INVENTION

This invention relates to improved methods and apparatus concerning exercise trainers.

BACKGROUND OF THE INVENTION

There are various devices known in the prior art for exercise trainers.

SUMMARY OF THE INVENTION

One or more embodiments of the present invention include a method. The method may include determining a plurality of heart rate sections for an individual, wherein each of the plurality of heart rate sections has an average beats per minute. The method may further include selecting a plurality of songs, wherein each of the plurality of songs has an average beats per minute approximately equal to an average beats per minute of one of the plurality of heart rate sections. The method may also include playing the plurality of songs in a sequence on a song playing device.

The plurality of songs may be selected by an individual based on the music preferences of the individual, the age of the individual, or for other reasons.

The plurality of songs may include a middle song, which is played in the middle of the sequence and which has an average beats per minute which is greater than the average beats per minute of all of the other songs of the plurality of songs. The plurality of songs may include one or more preceding songs which are played in the sequence so that they precede the middle song, and each of which has an average beats per minute which is less than the average beats per minute of the middle song. The plurality of songs may include one or more succeeding songs which are played in the sequence so that they succeed the middle song, and each of which has an average beats per minute which is less than the average beats per minute of the middle song.

The plurality of songs may be selected from a computer memory using a computer processor. The plurality of heart rate sections for the individual may be determined using a computer processor. The song playing device may be a compact disc player. The sequence may be stored in a computer memory.

The one or more preceding songs may include a first played song, and a second played song, with the second played song having a greater average beats per minute than the first played song. The one or more succeeding songs may include a first played after middle song, and a second played after middle song, with the first played after middle song having a greater average beats per minute than the first played song.

The method may further include determining a current heart rate in average beats per minute of the individual while the sequence of the plurality of songs is playing and while a particular song of the sequence of the plurality of songs is playing. The method may further include comparing the current heart rate with an average beats per minute of the particular song, and displaying on a computer monitor an indication of whether the current heart rate and the average beats per minute of the particular song are approximately equal. The method may further include displaying on a computer monitor an indication of whether the current heart rate is greater than or less than the average beats per minute of the particular song.

In one embodiment of the present invention a chart of the average beats per minute of each of the plurality of heart rate sections may be displayed on a computer monitor. The chart may include an arc shape.

At least one embodiment of the present invention includes an apparatus comprising a computer processor; and a song playing device. The song playing device may include the computer processor and a speaker device. The song playing device may include a compact disc player. The computer processor may be programmed to determine a plurality of heart rate sections for an individual, wherein each of the plurality of heart rate sections has an average beats per minute. The computer processor is programmed to assist an individual in selecting a plurality of songs, wherein each of the plurality of songs has an average beats per minute approximately equal to an average beats per minute of one of the plurality of heart rate sections. The computer processor may be programmed to play the plurality of songs in a sequence on a song playing device, wherein the sequence may be as previously described.

The computer processor may be programmed to select the plurality of songs from a computer memory. The computer processor may be programmed to determine the plurality of heart rate sections for the individual, and to cause them to be stored in the computer memory.

DETAILED DESCRIPTION OF THE DRAWINGS

Figure 1:
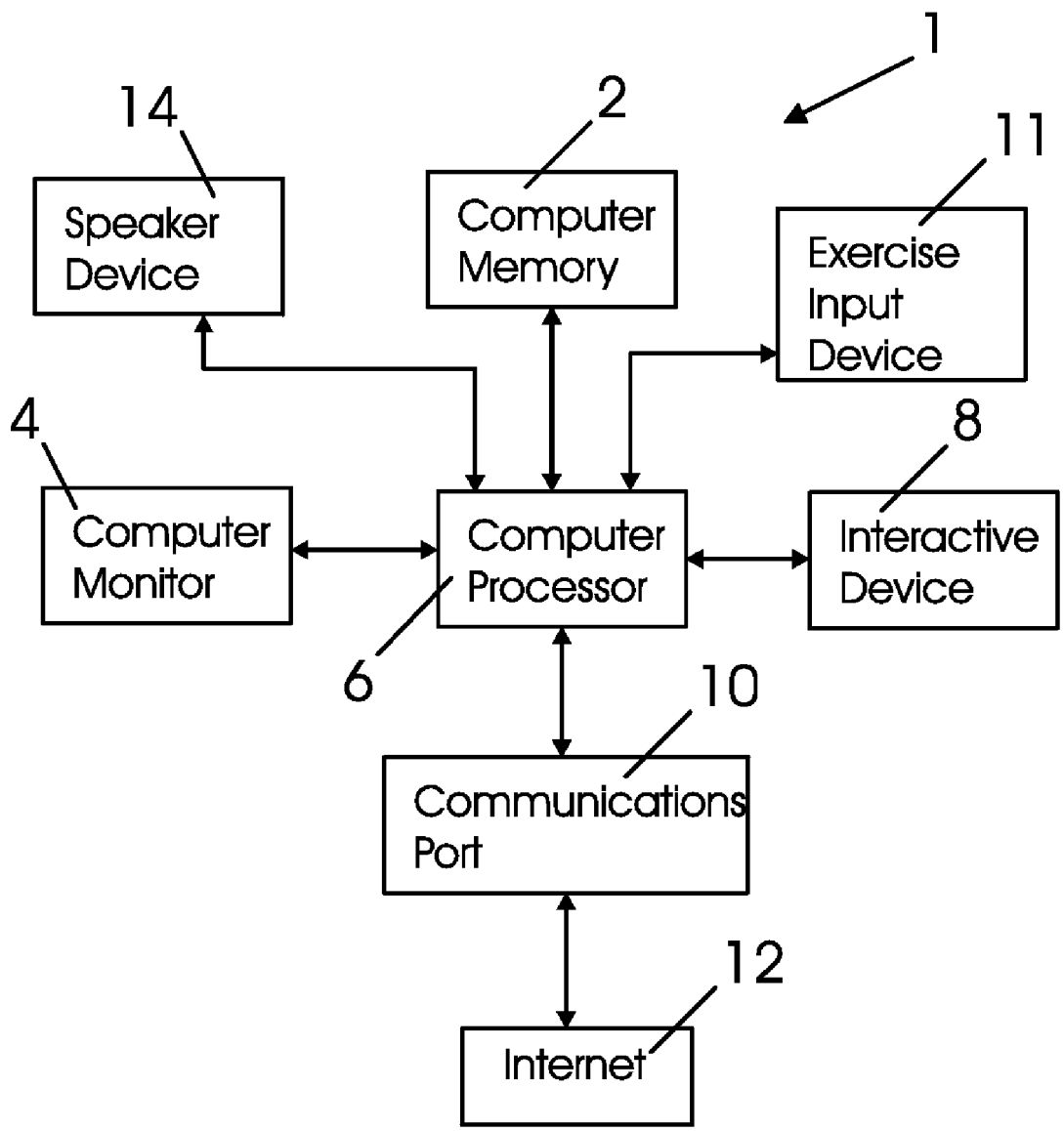
FIG. 1 shows block diagram of an apparatus for use in accordance with an embodiment of the present invention.

FIG. 1 shows block diagram of an apparatus 1 for use in accordance with an embodiment of the present invention. The apparatus 1 includes a computer memory 2, a computer monitor 4, a computer processor 6, an interactive device 8, a communications port 10, an exercise input device 11, the internet 12, and a speaker device 14. The computer processor 6 communicates with the computer memory 2, the computer monitor 4, the interactive device 8, the communications port 10, the exercise input device 11, and the speaker device 14 via communications links. The interactive device 8 may be comprised of a computer mouse, computer keyboard, and/or touch screen computer display. The speaker device 14 may be any type of sound emitting device than can receive signals from the computer processor 6 and emit sound. The speaker device 14 may be or may be replaced by head phones, and/or ear phones. The communications port 10 communicates with the internet 12 via communications links.

The exercise input device 11 may include, for example, a pedometer, a stationary bicycle, a device which measures the heart rate of an individual, a device which measures the cycle rate of an individual pedaling a bicycle, a device which measures the walking rate of an individual on a treadmill or running outside. The exercise input device 11 may provide information about the user's heart rate directly or by calculating the heart rate based on how fast the individual is operating a piece of exercise equipment, such as how fast the individual is pedaling a stationary bike or how fast the individual is walking on a treadmill or running outside.

Figure 2:
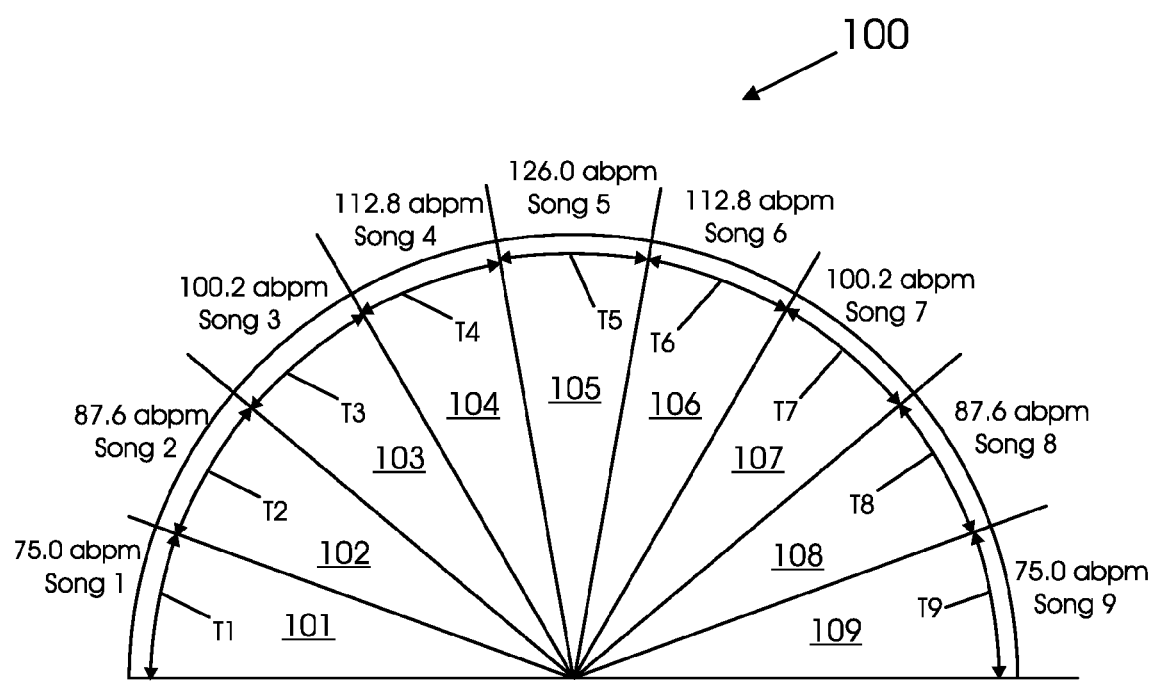
FIG. 2 shows chart of a plurality of songs and a plurality of corresponding average beats per minute for a plurality of heart rate sections for an individual human being in accordance with a method and apparatus of an embodiment of the present invention.

FIG. 2 shows chart 100, which can be displayed on the computer monitor 4 of FIG. 1, of a plurality of songs and a plurality of corresponding average beats per minute for a plurality of heart rate sections for an individual human being in accordance with a method and apparatus of an embodiment of the present invention. The chart 100 may be displayed in response to a request from a user using the interactive device 8 (or by mail) which may supply signals to the computer processor 6 which may cause the display of the chart 100. The chart 100 and/or information concerning the chart 100 may be stored in the computer memory 2 and may be retrieved by the computer processor 6.

The chart 100 shows heart rate sections 101, 102, 103, 104, 105, 106, 107, 108, and 109. In the example of FIG. 2, the heart rate sections 101-109 are approximately equal in size, however, in other embodiments they can be different in size. Each heart rate section, has a length of time. Heart rate sections 101-109 have length of times T1, T2, T3, T4, T5, T6, T7, T8, and T9 respectively. In the example of FIG. 2, each of the lengths of time of T1-T9 is equal to each of the other lengths of time of T1-T9, i.e. for example T1=T2=T3, etc. However, in other embodiments the lengths of time may be different. In the example of FIG. 2, each song of Song 1-Song 9, may be 3.5 to 4.0 minutes long, so that each time of T1-T9 may also be 3.5-4.0 minutes.

Each of the heart rate sections of 101-109 has a song which has an average number beats per minute ("abpm"). The average number of beats per minute may be the average number of drum beats per minute in the song or base beats per minute in the song. Heart rate sections 101, 102, 103, 104, 105, 106, 107, 108, and 109 have Song 1, Song 2, Song 3, Song 4, Song 5, Song 6, Song 7, Song 8, and Song 9, respectively. Song 1 has an average number of beats per minute of 75, while songs 2-9 have average number of beats per minute of 87.6, 100.2, 112.8, 126.0, 112.8, 100.2, 87.6, and 75, respectively. The songs of the song 1-song 9 are arranged in a sequence, so that the average number of beats per minute increases from the start to the middle of the sequence, from song 1 to the maximum of song 5, and then the average number of beats per minute decreases from the middle of the sequence, song 5, to the end of the sequence, song 9.

The sequence of song 1-song 9, with average number of beats per minute increasing from start to middle and then decreasing from middle to end works very well for work outs or exercise programs of a time duration approximately equal to a combined length of time of the nine songs (song 1-song 9). A person can exercise, for example using a stationary bicycle, or running with the use of a pedometer, so that his or her heart rate has an average number of beats per minute matching the average number of beats per minute of the particular song being played. For example, during the 3.5-4.0 minutes (T1) that song 1 is played, the individual may pedal a stationary bicycle or run so that their average number of beats per minute of their heart matches the average number of beats per minute of song 1, which in this case is 75 average beats per minute. When song 1 ends, song 2 is played, and the person can then increase their pedaling rate on the stationary bicycle or walking/running pace, and therefore their heart rate to match the average beats per minute of 87.6 of song 2. After song 2 ends, song 3 is played and the person would increase their pedaling on the stationary bicycle or pace if walking/running to get their heart rate to match to the 100.2 average beats per minute of song 3. The person would continue in this manner, pedaling/pacing in an appropriate manner, to get their hear rate to match, or approximately match, the average beats per minute of song 4, song 5, song 6, song 7, song 8, and song 9 in sequence.

The use of nine songs in FIG. 2, is done to provide at least a thirty minute cardiovascular workout, assuming an average song length of about 3.5 minutes. A workout of thirty-six minutes (nine times 4.0 minutes per song) may be preferred in one embodiment of the present invention (which in one example may result in an approximate walking/running distance or effective distance of three miles). More or less songs may be provided in alternative embodiments. The songs may be of unequal length in time in alternative embodiments.

Figure 3:
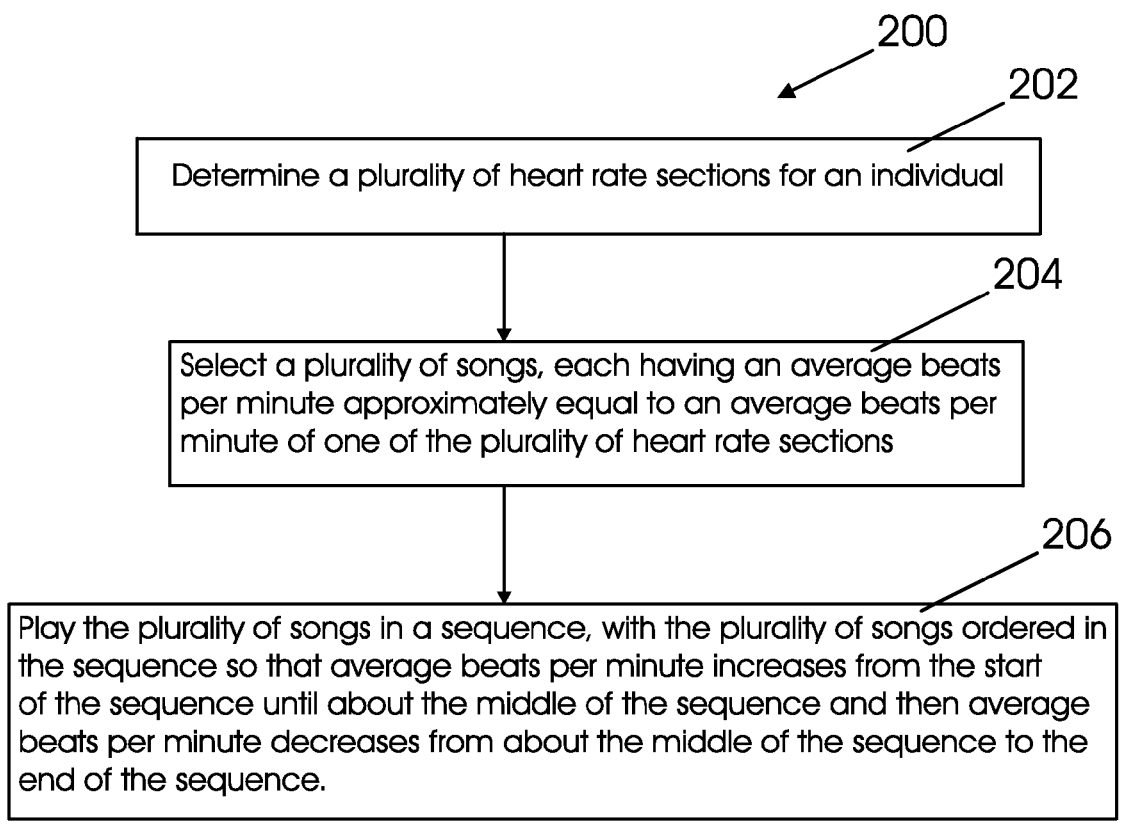
FIG. 3 shows a flow chart of a method in accordance with an embodiment of the present invention.

FIG. 3 shows a flow chart 200 of a method in accordance with an embodiment of the present invention. The method 200 includes step 202 at which a plurality of heart rate sections for an individual are determined. The heart rate sections may correspond to heart rate sections 101-109 of FIG. 2 and may be determined by computer processor 6 such as for example from data in computer memory 2, provided by internet 12, or provided by interactive device 8. Each heart rate section of 101-109 may have a number of beats per minute for a specific person's heart. At step 204 a plurality of songs, such as song 1-song 9, referred to in FIG. 2, are selected (in one example, based on a combination of an individual's music preferences i.e. artist, type—gospel, hip-hop, rock, classical, current, Motown oldies, etc).

Each of the plurality of songs has an average number of beats per minute approximately equal to one of the plurality of heart rate sections. For example, song 1 has an average number of beats per minute equal to 75.0 which is equal to an average number of beats per minute of the first heart rate section. At step 206, the plurality of songs, such as song 1 through song 9, are played in a sequence, with the plurality of songs ordered so that an average beats per minute increases from a start of the sequence, such as song 1 of FIG. 2, to a middle of the sequence, such as song 5 of FIG. 1, and then decreases from the middle of the sequence, such as song 5, to the end of the sequence, such as song 9.

Figure 4A:
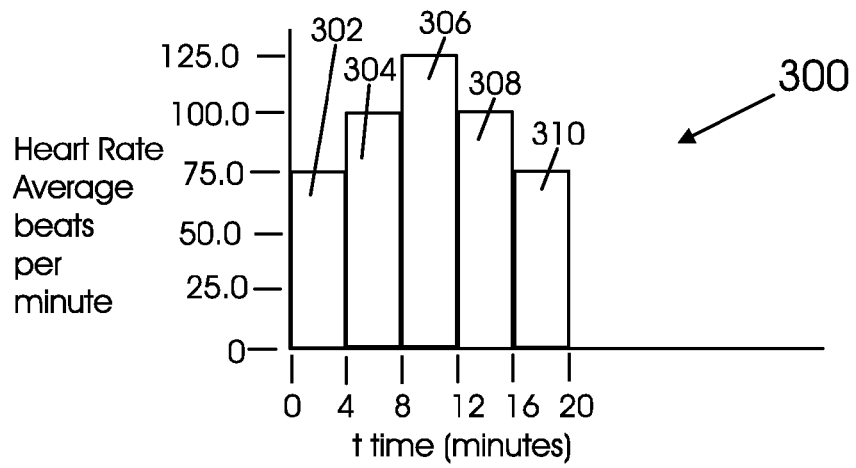
FIG. 4A shows a graph of heart rate average beats per minute with respect to time.

FIG. 4A shows a graph 300 of heart rate average beats per minute with respect to time, t, for an individual. The graph 300 may be displayed by computer processor 6 on the computer monitor 4, such as in response to user input using the interactive device 8 (or as an alternative the user inputs may be supplied via regular or snail mail and then may be input), or in response to input from the internet 12, or from the computer memory 2. The graph 300 shows bars or sections 302, 304, 306, 308, 310, and 312. The bars 302, 304, 306, 308, and 310 indicate that a person's heart rate is 75.0, 100.0, 125.0, 100.0, and 75.0 beats per minute, respectively, each rate continuing for about four minutes of time.

Figure 4B:
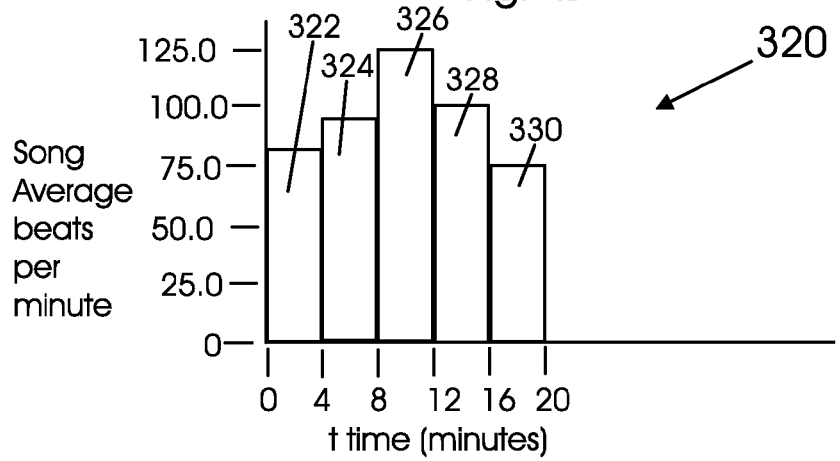
FIG. 4B shows a graph of song average beats per minute with respect to time.

FIG. 4B shows a graph 320 of song average beats per minute with respect to time, t. The graph 320 may be displayed by computer processor 6 on the computer monitor 4, such as in response to user input using the interactive device 8, or in response to input from the internet 12, or from the computer memory 2. The graph 320 shows bars or sections 322, 324, 326, 328, and 330. The bars 322, 324, 326, 328, and 330 indicate that a song's average beats per minute rate is 80.0, 95.0, 125.0, 100.0, and 75.0 beats per minute, respectively, each rate continuing for about four minutes of time.

Figure 4C:
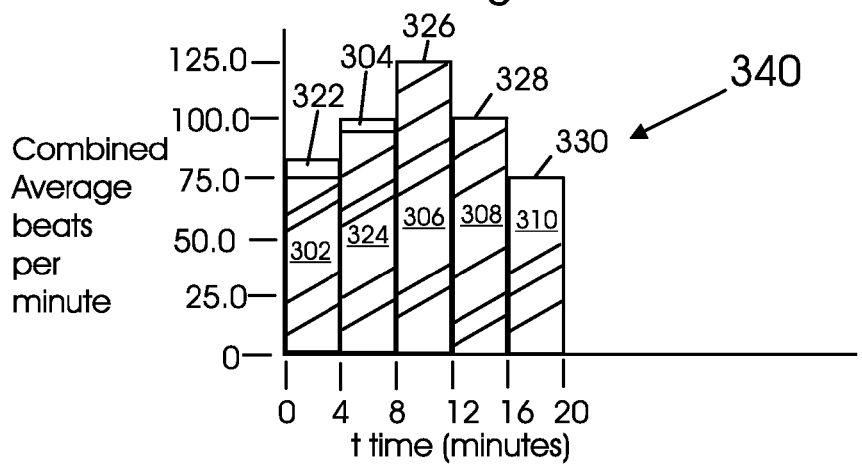
FIG. 4C shows a combined graph of song and heart rate average beats per minute with respect to time.

FIG. 4C shows a graph 340 of combined average beats per minute with respect to time, t. The graph 340 may be displayed by the computer processor 6 on the computer monitor 4, such as in response to user input using the interactive device 8, or in response to input from the internet 12, or from the computer memory 2. The graph 340 shows bars or sections 302, 304, 306, 308, and 310, laid on top of or overlaid by bars or sections 322, 324, 326, 328, and 330, respectively. If bar 302 is approximately equal to its corresponding bar 322 within a specified margin of error, then the combined bar 302 overlaid over 322 may be a specific color such as green, and if the two bars 302 and 322 are not within a margin of error (i.e. not approximately the same beats per minute or average beats per minute within a margin of error), then the bars 302 and 322 may be colored some other color by the processor 6. Similarly, if the bars 304 and 324, 306 and 326, 308 and 328, and 310 and 330 are within a margin of error (i.e. their average beats per minute are approximately equal) then the bars may be colored green and if not within a margin of error the bars may be colored some other color by the computer processor 6.

The present invention in one or more embodiments may use the existing technology of a music equalizer and pedometer for displaying the graphs of FIGS. 4A-4C or similar graphs. The line at the top of the bar 302 may be displayed in blue on a pedometer or on a computer monitor 4, and the line at the top of the bar 322 may be displayed in yellow on a music equalizer or computer monitor 4. The computer monitor 4 in conjunction with the computer processor 6 and/or interactive device 8 may function as a music equalizer or pedometer. When the bars 302 and 322 are approximately equal the yellow mixed with the blue may form green to indicate that bars 302 and 322 are approximately equal and therefore the beats per minute of the heart rate and the song are approximately equal. Similarly, the tops of bars 304, 306, 308, and 310 may also be displayed in blue and the tops of bars 324, 326, 328, and 330 may be displayed in yellow, so when they are superimposed as in FIG. 4C, a mixed green color indicates that the corresponding bars and corresponding average beats per minute are approximately equal, which indicates that the individual's heart rate and the song rate are within a range or approximately equal.

As an alternative embodiment, the bars 302, 304, 306, 308, and 310 may be displayed in blue, while the bars 322, 324, 326, 328, and 330 may be displayed in yellow. When the bars overlap as in FIG. 4C, the blue bars are larger than their corresponding yellow counterpart therefore, the color green will be seen with some blue at the top. If the yellow bars are larger than the blue counterparts, then the color green will be seen with some yellow at the top. For example, bar 302 (blue in one embodiment for FIG. 4A) and the bar 322 (yellow in one embodiment for FIG. 4B), are shown overlapped in FIG. 4C. Where the bar 302 and 322 cover each other as in the hatched or shaded area of FIG. 4C, a green color will appear from the mixture of blue and yellow. However, the bar 322 is larger than the bar 302, which means that the top area of bar 322 will not be covered by the bar 302 and the color yellow will be seen. The color yellow at the top in FIG. 4C for bar 322 (not mixed or covered by bar 302) indicates that the song average beats per minute are greater than the average heart rate beats per minute for the time zero to four minutes. This indicates that the song played from zero to four minutes has a faster beat rate than the person's heart rate. In this instance, in order to be in sync with the customized session, the individual must increase their pace.

On the other hand, bar 304 is greater than bar 324. Thus in FIG. 4C there is an area at the top of bar 304 which is not overlapped by bar 324, which will be colored blue. The area where bar 304 and 324 cover each other or mix together will be green. The blue at the top of bar 304 in FIG. 4C indicates that the heart rate beats per minute of the person is faster than the song rate beats per minute of the person during the song played in the four to eight minute time frame. In this instance, in order to be in sync with the customized session, the individual must decrease their pace.

The other pairs of bars, such as 306 and 326, 308 and 328, and 310 and 330, exactly coincide and therefore in FIG. 4C the area where they cover each other is green, and no blue or yellow would show at the top of overlapping bar pairs 306 and 326, 308 and 328, 310 and 330. In this instance, the individual is on target with the customized session.

A music sequence or sequence of songs as in FIG. 2, such as song 1 through song 9, can be stored on a music compact disc or in any other music storage medium (or presented as a program), such as a computer memory 2, and then can be played back for a customized, exercise program or workout.

The heart rate of 126.0 average beats per minute shown for heart rate section 105 in FIG. 2, may be a maximum heart rate which is predetermined, such as by using computer processor 6. The computer processor 6 may be programmed to determine the maximum heart rate in accordance with calculations disclosed in "Longitudinal Modeling of the Relationship between Age and Maximal Heart Rate", Gellish, et. al., copyright, 2007, by the American College of Sports Medicine. The maximum heart rate information may be provided from the internet 12, the interactive device 8, or the computer memory 2 to the computer processor 6. The computer processor 6, after receiving and/or calculating the maximum heart rate, may then determine a plurality of heart rates for heart rate sections before and after the maximum heart rate section. For example, the computer processor 6 may determine a heart rate of 89.5% of the maximum heart rate of 126.0 (for section 105 of FIG. 2), to obtain a heart rate of about 112.8 (as in sections 104 and 106 of FIG. 2) and then the computer processor 6 may use that 112.8 rate for a heart rate section before (section 104 of FIG. 2) and after (section 106 of FIG. 2) the maximum heart rate section (such as section 105 of FIG. 2).

In at least one embodiment of the present invention one beat per minute for a heart rate of a runner is approximately equal to 0.05 miles per hour.

In at least one embodiment of the present invention a sequence of a plurality of songs is stored in a music memory device or computer memory device (such as computer memory 2) such as a CD (compact disc) player. The plurality of songs is programmed, such as by a computer program (such as run by computer processor 6), or stored in the music memory to be played back in a specific sequence. The specific sequence starts out with a song with a low number of beats per minute, continues with further songs of a higher number of beats per minute, until about the middle of the sequence, where a middle (or peak) song with a peak number of beats per minute is played. The specific sequence continues, with a song with a lower number of beats per minute (than the peak song) following the middle (or peak song), and with songs of gradually decreasing number of beats per minute until the end of the specific sequence. In at least one embodiment of the present invention, after the music is stored in memory (such as computer memory 2) or programmed in the specific sequence, an exerciser needs only to playback the music in the specific sequence and exercise during the playback of the music in a manner to have the individual's heart rate beats per minute approximately match or mirror the beats per minute of the particular song of the sequence being played back. This allows the user to get a beneficial workout by gradually raising the individual's heart rate, in steps, to a peak, and then gradually lowering the individual's heart rate, in steps, from the peak. Once the customized session/workout/program has been performed as intended/mastered/attained (all songs indicate green), a new, updated session/workout/program can be created for the individual with increased bpm (beats per minute).

Although the invention has been described by reference to particular illustrative embodiments thereof, many changes and modifications of the invention may become apparent to those skilled in the art without departing from the spirit and scope of the invention. It is therefore intended to include within this patent all such changes and modifications as may reasonably and properly be included within the scope of the present invention's contribution to the art.

I claim:

1. A method comprising:
   determining a plurality of heart rate sections for an individual, wherein each of the plurality of heart rate sections has an average beats per minute;
   selecting a plurality of songs, wherein each of the plurality of songs has an average beats per minute approximately equal to an average beats per minute of one of the plurality of heart rate sections; and
   playing the plurality of songs in a sequence on a song playing device; and
   wherein the plurality of songs includes a middle song, which is played in the middle of the sequence and which has an average beats per minute which is greater than the average beats per minute of all of the other songs of the plurality of songs;
   wherein the plurality of songs includes one or more preceding songs which are played in the sequence so that they precede the middle song, and each of which has an average beats per minute which is less than the average beats per minute of the middle song; and
   wherein the plurality of songs includes one or more succeeding songs which are played in the sequence so that they succeed the middle song, and each of which has an average beats per minute which is less than the average beats per minute of the middle song.

2. The method of claim 1 wherein
   the plurality of songs are selected from a computer memory using a computer processor.

3. The method of claim 1 wherein
   the plurality of heart rate sections for the individual are determined using a computer processor.

4. The method of claim 1 wherein
   the song playing device is a compact disc player.

5. The method of claim 1 wherein
   the sequence is stored in a computer memory.

6. The method of claim 1 wherein
   the one or more preceding songs include a first played song, and a second played song, with the second played song having a greater average beats per minute than the first played song; and
   wherein the one or more succeeding songs include a first played after middle song, and a second played after middle song, with the first played after middle song having a greater average beats per minute than the first played song.

7. The method of claim 1 further comprising
   determining a current heart rate in average beats per minute of the individual while the sequence of the plurality of songs is playing and while a particular song of the sequence of the plurality of songs is playing;
   comparing the current heart rate with an average beats per minute of the particular song;
   displaying on a computer monitor an indication of whether the current heart rate and the average beats per minute of the particular song are approximately equal.

8. The method of claim 7 further comprising
   displaying on a computer monitor an indication of whether the current heart rate is greater than the average beats per minute of the particular song.

9. The method of claim 7 further comprising
   displaying on a computer monitor an indication of whether the current heart rate is less than the average beats per minute of the particular song.

10. The method of claim 1 further comprising
    displaying on a computer monitor a chart of the average beats per minute of each of the plurality of heart rate sections.

11. An apparatus comprising:
    a computer processor; and
    a song playing device;
    wherein the computer processor is programmed to determine a plurality of heart rate sections for an individual, wherein each of the plurality of heart rate sections has an average beats per minute;
    wherein the computer processor is programmed to assist an individual in selecting a plurality of songs, wherein each of the plurality of songs has an average beats per minute approximately equal to an average beats per minute of one of the plurality of heart rate sections; and
    wherein the computer processor is programmed to play the plurality of songs in a sequence on a song playing device; and
    wherein the plurality of songs includes a middle song, which is played in the middle of the sequence and which has an average beats per minute which is greater than the average beats per minute of all of the other songs of the plurality of songs;
    wherein the plurality of songs includes one or more preceding songs which are played in the sequence so that they precede the middle song, and each of which has an average beats per minute which is less than the average beats per minute of the middle song; and
    wherein the plurality of songs includes one or more succeeding songs which are played in the sequence so that they succeed the middle song, and each of which has an average beats per minute which is less than the average beats per minute of the middle song.

12. The apparatus of claim 11 further comprising
    a computer memory; and
    wherein the computer processor is programmed to select the plurality of songs from a computer memory.

13. The apparatus of claim 11 further comprising
    a computer memory; and
    wherein the computer processor is programmed to determine the plurality of heart rate sections for the individual, and to cause them to be stored in the computer memory.

14. The apparatus of claim 11 wherein
    the song playing device is a compact disc player.

15. The apparatus of claim 11 further comprising
    a computer memory; and
    wherein the sequence is stored in the computer memory.

16. The apparatus of claim 11 wherein
    the one or more preceding songs include a first played song, and a second played song, with the second played song having a greater average beats per minute than the first played song; and
    wherein the one or more succeeding songs include a first played after middle song, and a second played after middle song, with the first played after middle song having a greater average beats per minute than the first played song.

17. The apparatus of claim 11 further comprising
a computer monitor; and
wherein the computer processor is programmed to determine a current heart rate in average beats per minute of the individual while the sequence of the plurality of songs is playing and while a particular song of the sequence of the plurality of songs is playing;
the computer processor is programmed to compare the current heart rate with an average beats per minute of the particular song;
the computer processor is programmed to display on the computer monitor an indication of whether the current heart rate and the average beats per minute of the particular song are approximately equal.

18. The apparatus of claim 17 wherein
the computer processor is programmed to display on the computer monitor an indication of whether the current heart rate is greater than the average beats per minute of the particular song.

19. The apparatus of claim 17 wherein
the computer processor is programmed to display on the computer monitor an indication of whether the current heart rate is less than the average beats per minute of the particular song.

20. The apparatus of claim 17 wherein
the computer processor is programmed to display on the computer monitor a chart of the average beats per minute of each of the plurality of heart rate sections.

* * * * *